(12) United States Patent
Shoaf

(10) Patent No.: US 6,815,178 B1
(45) Date of Patent: Nov. 9, 2004

(54) ENDOSPORE DETECTION METHOD

(76) Inventor: Antony R. Shoaf, 2386 Horseshoe Neck Rd., Lexington, NC (US) 27295

( * ) Notice: Subject to any disclaimer, the term of this patent is extended or adjusted under 35 U.S.C. 154(b) by 467 days.

(21) Appl. No.: 10/035,277

(22) Filed: Nov. 19, 2001

(51) Int. Cl.[7] .................................................. C12Q 1/04
(52) U.S. Cl. ............................................ 435/34; 435/30
(58) Field of Search .............................. 435/34, 30, 31, 435/252.5, 832; 436/172

(56) References Cited

U.S. PATENT DOCUMENTS 5,876,960 A * 3/1999 Rosen .......................... 435/39
6,232,107 B1 * 5/2001 Bryan et al. ................. 435/189

OTHER PUBLICATIONS

Rajan K. Chelation Characteristics of Calcium in Relation to Water Binding and Heat Resistance of Bacterial Endospores. Spore Research vol. 2, 527–543, 1977.*
Shimomura O. Effect of Calcium Chelators on the Ca+2 Dependent Luminescence of Aequorin. Biochem J 221(3)907–910, 1984.*
"Regeneration of the photoprotein aequorin" by Nature vol. 256 Jul. 17, 1975 pp. 236–238.
Methods in Cell Biology (R. Nuccitelli, Ed), 1994, vol. 40, pp. 305–338 Academic Press, Orlando, FL.
Article published in IEEE Engineering in Medicine and Biology, Sep./Oct. 2002 issue, Elizabeth D. Lester and Adrian Ponce, *An Anthrax "Smoke" Detector*, pp. 38–42.
Article on Elizabeth Lester found on www.jpl.nasa.gov web site, published Oct. 23, 2002, *College Student's Curiosity Leads to Discovery*, 2 pages.
Article found on www.jpl.nasa.gov web site, published Oct. 23, 2002, *NASA to Develop Biohazard "Smoke" Detector*, 2 pages.
Article found on www.nasatech.com web site, published under the NASA Tech Briefs, Jan. 2003, *NASA Biohazard Monitor Mimics a Smoke Detector*, 1 page.
Microbiology an Introduction, 7th Edition, copyright 2001, pp. 97–98.
Biology of Microorganisms, 9th Edition, copyright 2000, pp. 91–95.
Proc. Natl. Acad. Sci. USA, vol. 75, No. 6, pp. 2611–2615, Jun. 1978.
Proc. Natl. Acad. Sci, USA, vol. 96, pp. 157–161, Jan. 1999.
Analytical Biochemistry 29, pp. 381–392 (1969).

* cited by examiner

*Primary Examiner*—Ralph Gitomer

(57) ABSTRACT

The invention herein provides for the detection of certain calcium containing endospores, and particularly pertains to the detection of bacillus anthracis by first chelating calcium ions of said endospores and then reacting the chelated calcium ions with aequorin to generate a light pulse which can then be detected by a standard liquid scintillation spectrometer.

20 Claims, 2 Drawing Sheets

ENDOSPORE DETECTION METHOD

FIELD OF THE INVENTION

The invention herein pertains to detection devices and methods, and particularly pertains to the detection of calcium containing endospores which are delivered from an airborne state to a reaction vessel.

DESCRIPTION OF THE PRIOR ART AND OBJECTIVES OF THE INVENTION

Certain light emitting photoproteins, such as those isolated from the jellyfish Aequorea aequoorea, perform a natural reaction when allowed to mix with calcium ion, $Ca^{++}$, with the resultant production of light or chemiluminescence. Such calcium reporter photoproteins are known as aequorin.

Many gram-positive bacteria such as those of the genera *Clostridium* and *Bacillus* form specialized "resting" cells called endospores. Endospores are highly durable dehydrated cells with thick walls and additional layers. They are formed internal to the bacterial cell membrane.

When released into the environment, endospores can survive extreme heat, lack of water and exposure to many toxic chemicals and radiation. Most of the water present in the spore cytoplasm is eliminated. Such endospores do not generally carry out metabolic reactions. A strikingly large amount of an organic acid called dipicolinic acid (found in the cytoplasm), is accompanied by a large number of calcium ions. Calcium ions ($Ca^{++}$) are combined with the dipicolinic acid as seen below:

$$\left[ \begin{array}{c} \text{structure with } Ca^{++} \end{array} \right]_n$$

The calcium-dipicolinic acid complex represents about ten percent of the dry weight of the endospore. As would be understood, such endospores can readily become airborne. If present in an area of human occupancy, such as an office building, home or the like, certain endospores can be life threatening when present through inadvertence, accident or deliberately introduced by bioterrorists.

Liquid scintillation spectrometers are commonly used to measure radioisotopes such as in medical research when used in an out of coincidence mode it senses both analog signals from two photomultiplier tubes to thereby act as a photon (light pulse) counter.

While various types of detection methods for certain deadly endospores such as *Bacillus anthracis* (anthrax) are known, these methods generally consist of collecting specimens from office buildings, homes or the like and thereafter delivering them to a laboratory for analysis. While such laboratory analyses may be very accurate, they are time consuming in that the collection, delivery and analytical work can take several days. Thus, those unfortunate enough to be infected with deadly endospores such as anthrax may have their medical condition diagnosed too late to save their lives.

Therefore, in view of the need for a speedy and continuous method of detecting anthrax and other calcium containing endospores which may be, for example, airborne in public buildings, the present invention was conceived and one of its objectives is to provide a device and method whereby bacillus anthracis and other calcium containing endospores can be easily and inexpensively detected.

It is an objective of the invention to provide a device for detecting certain calcium containing endospores when used as weapons or when naturally occurring such as near cattle or other animals.

It is another objective of the present invention to provide a device and method for detecting certain calcium containing endospores which is easy to operate and requires little specialized training.

It is yet another objective of the present invention to provide a method for detecting calcium containing endospores which is relatively inexpensive, to operate continuously for twenty-four hours a day.

It is still another objective of the present invention to provide a method of detecting calcium containing endospores utilizing a chelating agent and natural aequorin as derived from jellyfish.

It is still another objective of the present invention to provide a method of detection of calcium containing endospores utilizing a standard scintillation spectrometer.

Various other objectives and advantages of the present invention will become apparent to those skilled in the art as a more detailed description is set forth below.

SUMMARY OF THE INVENTION

The aforesaid and other objectives are realized by providing a scintillation spectrometer with a reaction vessel containing a chemiluminescent liquid. The reaction vessel is joined to an air pump by an intake conduit. The air pump delivers air from an office, room or the like through a conventional particulate filter capable of excluding particles greater than 20 $\mu M$, and into the chemiluminescent liquid. Calcium containing endospores such as *Bacillus anthracis* then mix with the chemiluminescent liquid in which the calcium ions contained therein are first chelated. The chelated calcium ions then react with the chemiluminescent photoprotein aequorin in the chemiluminescent liquid and produce light. This chemiluminescent reaction emits photons of light which, in one embodiment are directed through the walls of the glass reaction vessel, through a light guide and into photomultiplier tubes where they are intensified. Analog signals resulting therefrom are then delivered to a ratemeter which in turn delivers corresponding electrical signals to a chart recorder and, if desired, to a printer.

In a second embodiment of the invention the spectrometer converts the light pulses to a digital signal which are sent to a personal computer (PC) whereby the signals can be read in real time on the PC monitor.

DETAILED DESCRIPTION OF THE PREFERRED EMBODIMENTS AND OPERATION OF THE INVENTION

Figure 1:
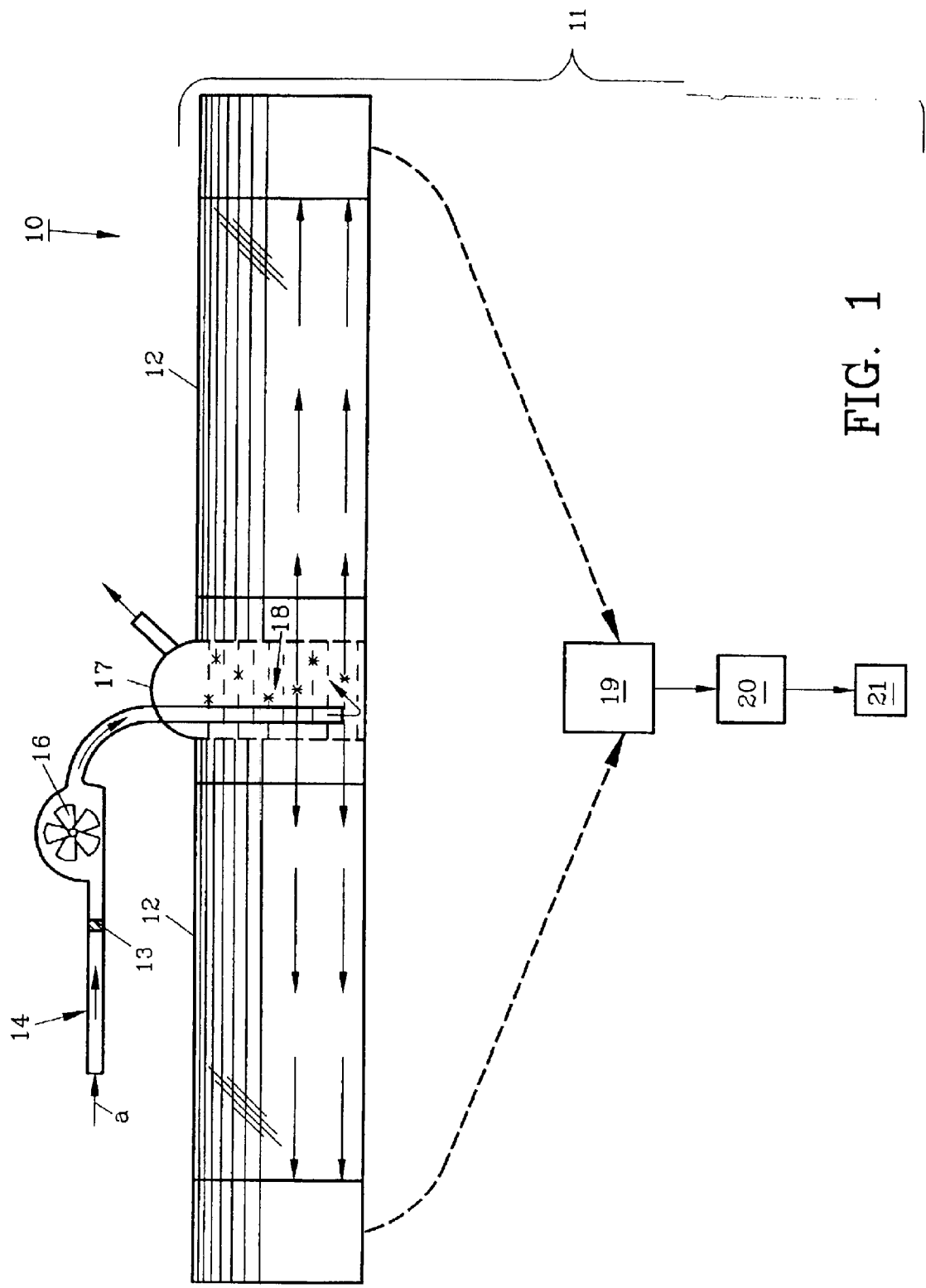
FIG. 1 shows a schematic representation of the preferred detection device of the invention.

For detection of endospores of *Bacillus anthracis* capable of causing a disease, commonly known as anthrax, the preferred method is demonstrated in FIG. 1 whereby air with calcium containing endospores is represented by arrow a. Preferred device 10 for detecting endospores is shown in schematic fashion utilizing a model 3320 Packard Liquid Scintillation spectrometer 11 as sold by Packard Instrument Company of Downers Grove, Ill. operated in an out-of-coincidence mode at the preferred ambient temperature of 22° C. Device 10 is used for continuous monitoring of analog signals received from each of the photomultiplier tubes 12, 12'.

As seen, calcium containing endospores are first directed through particulate filter 13 (capable of removing particle size of 20 μM) of air tube 14 by air pump 15 which then forces the filtered air through intake conduit 16 and on into reaction vessel 17. Conventional particulate filter 13 excludes particles greater than 20 μM (1 μM=0.000001M).

As shown in FIG. 1, reaction vessel 17 contains preferred chemiluminescent liquid 18 which is prepared as follows:

7.455 g. of potassium chloride, 1.047 g. 3-[-Morpholino]propanesulfonic acid, and 19.01 mg. ethylenediamine tetraacetate, tetrasodium salt, (EDTA)

are dissolved in 1 liter of water and are mixed to form the preferred buffer solution.

Next, 1 g. aequorin* and 100 ml of the buffer solution above are mixed and approximately 20 ml of this preferred chemiluminescent liquid 18 are placed in reaction vessel 17. Preferably naturally occurring aequorin is used but purified extracts of natural aequorin or synthetically prepared aequorin may also be used.

*Natural aequorin can be purchased from Sigma Co. of St. Louis, Mo. 63178.

Reaction vessel 17, as manufactured by Fisher Scientific of Pittsburgh, Pa. 15275, is preferably made of quartz while borosilicate low potassium glass may also be used. Reaction vessel 17 preferably has a height of 61 mm and an outside diameter of 28 mm. Air pump 15 as shown preferably provides a 12.5L/min air flow to reaction vessel 17 through Teflon (trademark of E.I. DuPont DeNemours and Co., Wilmington, Del.), intake conduit 16 which has a diameter of 4 mm. As would be further understood from FIG. 1, light pulses from reaction vessel 17 are directed through photomultiplier tubes 12, 12' and are directed to ratemeter 19, preferably a model 280A as manufactured by Packard Instrument Company. The light pulses generated in reaction vessel 17 are a result of the chemical reactions shown below:

$$Ca^{++} \text{ endospores} + EDTA \rightarrow Ca^{++}$$

$$Ca^{++} + \text{aequorin} \rightarrow \text{photons of light}$$

Signals are sent from ratemeter 19 as illustrated schematically in FIG. 1 to Honeywell Electronik strip chart recorder 20 and on to Monroe digital printer 21. Separate count per minute readings can be then printed as desired. While a model 3320 Packard Instrument liquid scintillation spectrometer is preferred, various other types of spectrometers could likewise be used.

Standard scintillation spectrometer 11 as seen in FIG. 1 includes photomultiplier tubes 12, 12' which are preferably manufactured by EMI Thorn Company, (England) as catalogue No. 9635QB. Tubes 12, 12' are sensitive to the wavelengths of light corresponding to the maximum wavelength of light emissions provided herein.

Figure 2:
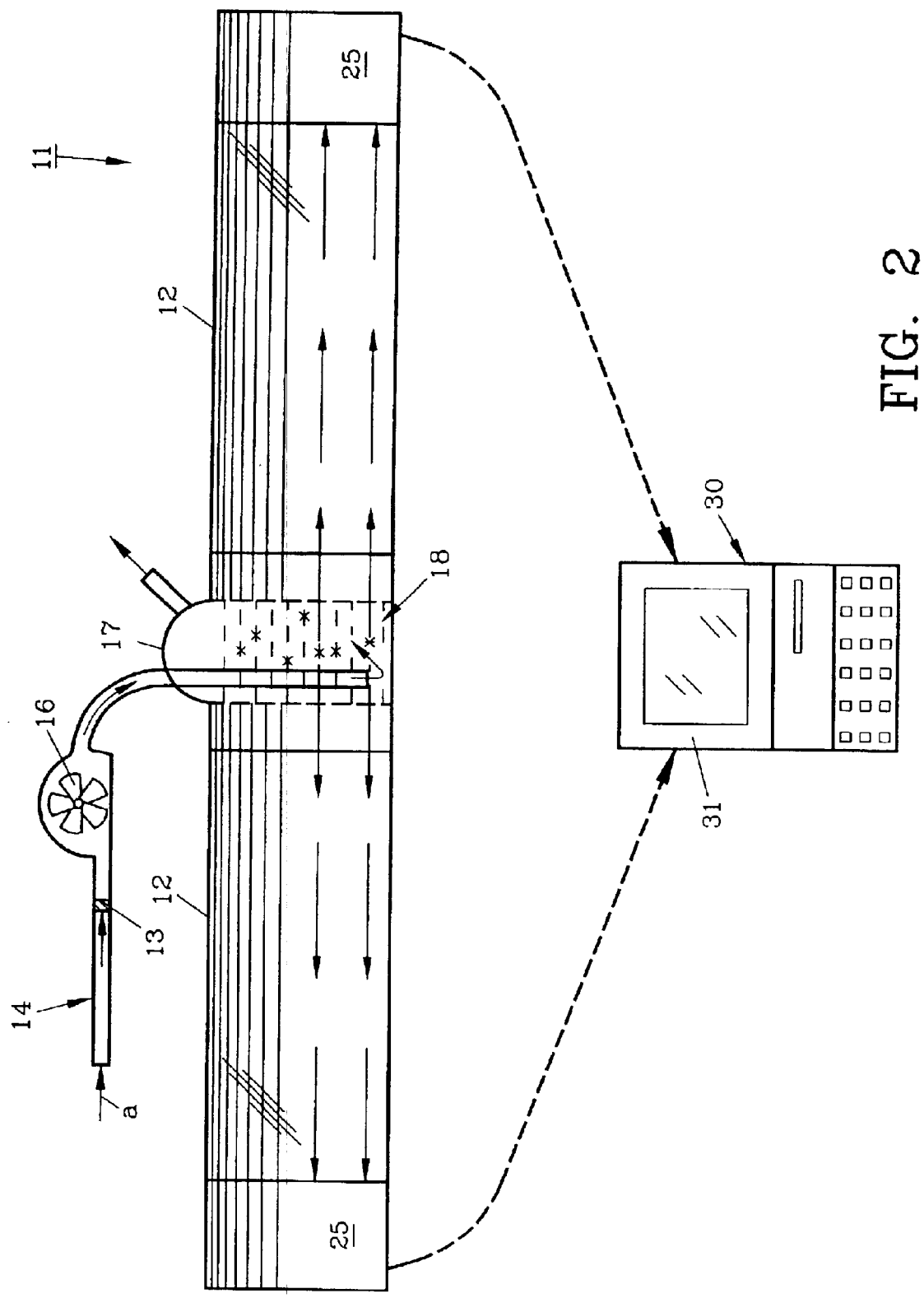
FIG. 2 demonstrates schematically an alternate embodiment of the invention as shown in FIG. 1.

In an alternate embodiment as shown in FIG. 2, Packard spectrometer 11 has been modified as schematically shown in FIG. 2 whereby its analog to digital convertor 25 is utilized and the resulting digital signal is fed to PC 30. PC monitor 31 can then be used to continuously monitor the activity of reaction vessel 17 in real time.

While the preferred detection device 10 as shown in FIG. 1 is suitable for use as a table or desktop setup, device 10 could also be made portable and carried by a person. In this event the device would be miniaturized to some degree and have its own power source such as conventional batteries. A miniaturized version (not seen) may have dimensions of about 60 cm by 30 cm by 30 cm for portability.

The illustrations and examples provided herein are for explanatory purposes and are not intended to limit the scope of the appended claims.

I claim:

1. A method of detecting the presence of calcium containing endospores comprising the steps of:
   a) directing calcium containing endospores into a chemiluminescent liquid;
      i) chelating the calcium of said endospores; and
      ii) reacting the chelated calcium to produce a light pulse; and
   b) detecting the light pulse; and
   c) correlating the light pulse with the presence of calcium containing endospores.

2. The method of claim 1 wherein detecting calcium containing endospores comprises the step of detecting endospores of the *Bacillus* genera.

3. The method of claim 1 wherein detecting calcium containing endospores comprises the step of detecting endospores of the *Clostridium* genera.

4. The method of claim 2 wherein detecting *Bacillus* genera endospores comprises the step of detecting endospores of the species *Bacillus anthracis*.

5. The method of claim 1 wherein chelating the calcium comprises the step of chelating the calcium with ethylenediamine tetraacetate.

6. The method of claim 1 wherein reacting the chelated calcium comprises the step of reacting the calcium with aequorin.

7. The method of claim 1 wherein directing calcium containing endospores into a chemiluminescent liquid comprises the further steps of:
   a) pumping air comprising calcium containing endospores through a particulate filter to remove particles greater than 20 μM; and
   b) directing the filtered air into a reaction vessel containing the chemiluminescent liquid.

8. The method of claim 1 wherein detecting the generated light comprises the further step of: directing the light pulse through a light guide to a spectrometer for converting the light pulse into an electronic signal.

9. The method of claim 8 further comprising the step of: sending the electronic signal to a personal computer for viewing and analyzing by a user.

10. The method of claim 8 further comprising the step of: sending the electronic signal to a chart recorder for recording the quantity of light generated.

11. A method of detecting the presence of calcium containing endospores with an air pump, a particulate filter, a reaction vessel, and a spectrometer comprising the steps of:
   a) pumping air comprising calcium containing endospores with the air pump into the reaction vessel containing a calcium chelating agent and a chemiluminescent photoprotein,
   b) reacting the calcium containing endospores with the calcium chelating agent to chelate calcium ions,
   c) reacting the chelated calcium ions with the chemiluminescent photoprotein to generate photons of light, d) directing the photons of light to the spectrometer, e) converting the photons of light to an electronic signal, f) recording the electronic signal, and g) correlating the electronic signal with the presence of calcium containing endospores.

12. The method of claim 11 wherein pumping air into the reaction vessel comprises the further step of: pumping air through the particulate filter to remove particles greater than 20 $\mu$M.

13. The method of claim 12 wherein filtering the air comprises the further step of: pumping the air at a rate of approximately 12.5 L/min.

14. The method of claim 11 wherein pumping calcium containing endospores into the reaction vessel containing a chemiluminescent liquid comprises the further steps of:

a) dissolving 7.455 g of potassium chloride, 1.047 g of 3-[Morpholino]propanesulfonic acid and 19.01 mg of ethylenediamine tetraacetate tetrasodium salt in 1 L of water to form a buffer solution, b) mixing 100 ml of the buffer solution with 1 g of aequorin to form the chemiluminescent liquid, and c) inserting 20 ml of the chemiluminescent liquid in the reaction vessel comprising quartz.

15. The method of claim 11 wherein reacting the calcium containing endospores with the calcium chelating agent comprises the further step of: reacting the calcium containing endospores with ethylenediamine tetraacetate tetrasodium salt.

16. The method of claim 11 wherein reacting the chelated calcium ions with the chemiluminescent photoprotein comprises the further step of: reacting the chelated calcium ions with aequorin.

17. The method of claim 11 wherein reacting the chelated calcium ions with the chemiluminescent photoprotein comprises the further step of: reacting the chelated calcium ions with natural aequorin.

18. The method of claim 11 further comprising the step of: counting the photons of light by directing them to a liquid scintillator spectrometer.

19. The method of claim 11 wherein recording the electronic signal comprises the further step of: sending the electronic signal to a personal computer.

20. The method of claim 19 wherein sending the electronic signal comprises the further step of: sending the electronic signal to a chart recorder.

* * * * *